United States Patent [19]
Koike et al.

[11] Patent Number: 5,130,477
[45] Date of Patent: Jul. 14, 1992

[54] OLIGOHEXAFLUOROPROPYLENE OXIDE DERIVATIVES AND METHOD OF MAKING

[75] Inventors: Noriyuki Koike, Tano; Masayuki Oyama, Gunma; Toshio Takago, Annaka, all of Japan

[73] Assignee: Shin-Etsu Chemical Company Limited, Tokyo, Japan

[21] Appl. No.: 748,613

[22] Filed: Aug. 22, 1991

[30] Foreign Application Priority Data

Aug. 23, 1990 [JP] Japan ................................ 2-222089

[51] Int. Cl.$^5$ ............................................. C07C 51/58
[52] U.S. Cl. ................................... 562/840; 562/856
[58] Field of Search .......................... 562/840, 856

[56] References Cited

U.S. PATENT DOCUMENTS

| | | | |
|---|---|---|---|
| 2,713,593 | 7/1955 | Brice et al. | 562/840 |
| 3,274,239 | 9/1966 | Selman | 562/840 |
| 3,644,501 | 2/1972 | Parre et al. | 562/856 |
| 3,678,068 | 7/1972 | Anello et al. | 562/840 |
| 3,697,564 | 10/1972 | Anello et al. | 562/840 |
| 3,706,773 | 12/1972 | Anello et al. | 562/840 |

*Primary Examiner*—Paul J. Killos
*Attorney, Agent, or Firm*—Millen, White & Zelano

[57] ABSTRACT

A novel oligohexafluoropropylene oxide derivative is a useful intermediate. It is prepared by reacting an oligohexafluoropropylene oxide carbonyl fluoride with a metal iodide.

2 Claims, 2 Drawing Sheets

OLIGOHEXAFLUOROPROPYLENE OXIDE DERIVATIVES AND METHOD OF MAKING

This invention relates to a novel oligohexafluoropropylene oxide derivative and a method for preparing the same.

BACKGROUND OF THE INVENTION

Iodine-containing oligohexafluoropropylene oxides of the general formula (IV):

(IV)

wherein Rf is a perfluoroalkyl group having 1 to 10 carbon atoms and letter n is an integer of from 0 to 100 are useful intermediates for use in the synthesis of fluoro resins, fluoro rubbers and fluoro surfactants. However, none of prior art methods for preparing such oligohexafluoropropylene oxides have gained commercial success.

More particularly, iodine-containing oligohexafluoropropylene oxides are prepared as shown by the following reaction scheme by starting with an oligohexafluoropropylene oxide carbonyl fluoride of the following formula (II), subjecting the reactant to hydrolysis to form a carboxylic acid, reacting it with silver oxide to form a silver salt, and subjecting the salt to pyrolysis in the presence of iodine to thereby form an iodine-containing oligohexafluoropropylene oxide of the following formula (IV) (see Japanese Patent Application Kokai No. 30441/1988).

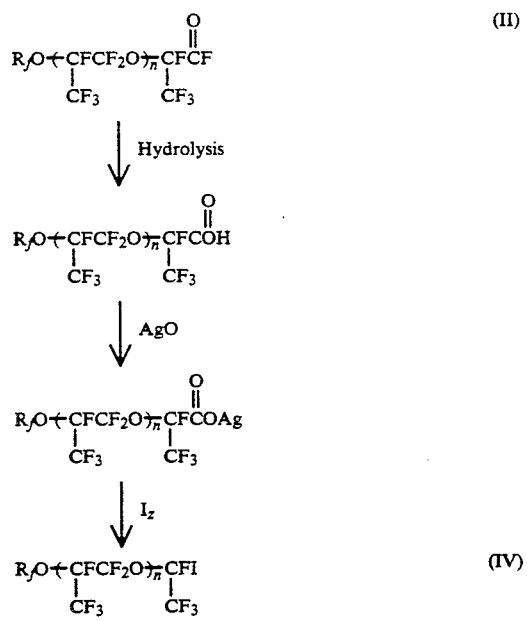

However, several problems must be solved before this process can be commercially practiced. The end product, iodine-containing oligohexafluoropropylene oxide is recovered only in yields of about 70 to 85%. The intermediate or silver salt is often a solid which is difficult to handle. The use of expensive silver necessitates silver recovery from a commercial standpoint. The overall process involves three steps, during which toxic hydrogen fluoride evolves. Pyrolysis reaction must be carried out before the end product can be obtained. Also, economical problems arise from the use of expensive reactants and increased installation cost.

There is a need for the commercially advantageous manufacture of iodine-containing oligohexafluoropropylene oxides while overcoming the above-mentioned problems.

SUMMARY OF THE INVENTION

We have found that by reacting an oligohexafluoropropylene oxide carbonyl fluoride of the general formula (II):

(II)

wherein Rf is a perfluoroalkyl group having 1 to 10 carbon atoms and letter n is an integer of from 0 to 100 with a metal iodide of the general formula (III):

(III)

wherein M is a metal atom and letter a is the valence of the metal atom, a novel oligohexafluoropropylene oxide derivative having a carbonyl iodide group of the general formula (I):

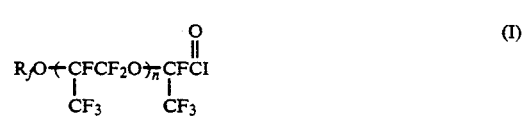

(I)

wherein Rf and n are as defined above is obtained in high yields. The reaction proceeds in a simple manner even at atmospheric pressure and room temperature without forming a by-product. The resulting derivative releases carbon monoxide upon exposure to ultraviolet light at atmospheric pressure and room temperature and converts into an iodine-containing oligohexafluoropropylene oxide of formula (IV) at a conversion rate of 95% or higher.

That is, an iodine-containing oligohexafluoropropylene oxide of formula (IV) can be prepared from an oligohexafluoropropylene oxide carbonyl fluoride of formula (II) by way of a novel oligohexafluoropropylene oxide derivative of formula (I) as an intermediate. As compared with the prior art process, this process has many advantages.

(1) Very high yield.
(2) No use of expensive silver oxide.
(3) A simplified process consisting of two steps.
(4) No evolution of toxic hydrogen fluoride during the process.
(5) Low reaction temperature.
(6) The intermediate or oligohexafluoropropylene oxide derivative of formula (I) is liquid at room temperature and can be isolated by distillation if it has a low molecular weight.
(7) The second step of ultraviolet exposure requires merely to irradiate ultraviolet light while no other special operation is needed. The reaction system can be increased to any desired scale in theory insofar as a tank for receiving the reaction solution is installed in the system.

Since the iodine-containing oligohexafluoropropylene oxide of formula (IV) can be prepared in this way with many commercial benefits, the oligohexafluoropropylene oxide derivative of formula (I) is a useful intermediate for the synthesis of the compound of formula (IV).

Therefore, the present invention in one aspect provides an oligohexafluoropropylene oxide derivative of formula (I) as defined above. In another aspect, the present invention provides a method for preparing an oligohexafluoropropylene oxide derivative of formula (I) by reacting an oligohexafluoropropylene oxide carbonyl fluoride of formula (II) with a metal iodide of formula (III) as defined above.

DETAILED DESCRIPTION OF THE INVENTION

Figure 1:
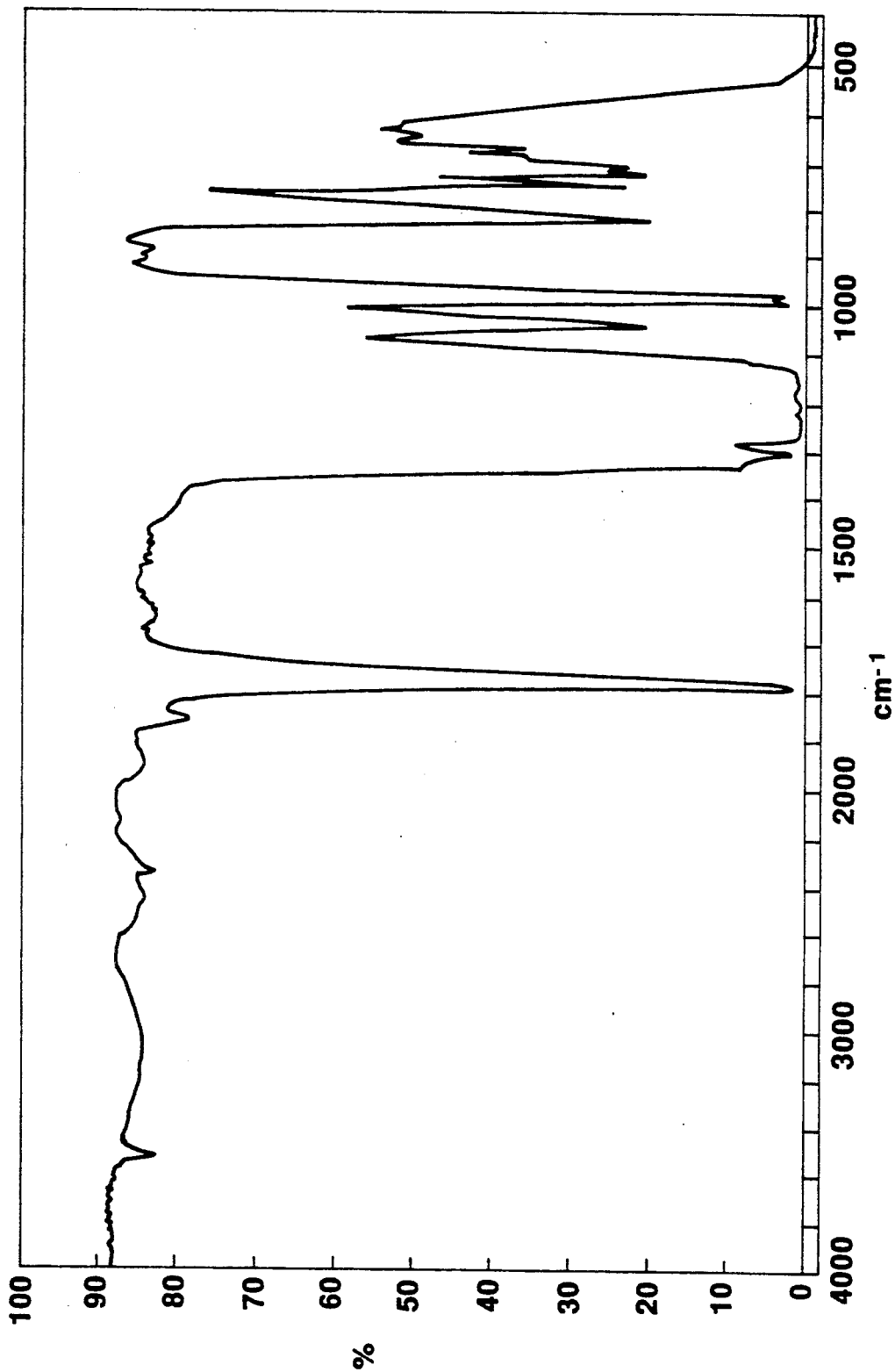
FIG. 1 is a chart showing the IR spectrum of an oligohexafluoropropylene oxide derivative obtained in Example.

The oligohexafluoropropylene oxide derivatives of the present invention are compounds having a carbonyl iodide group as represented by the general formula (I):

(I)

In formula (I), Rf is a perfluoroalkyl group having 1 to 10 carbon atoms, for example, trifluoromethyl, pentafluoroethyl, heptafluoropropyl, and heptafluoroisopropyl groups. Letter n is an integer of from 0 to 100, preferably from 0 to 30.

The oligohexafluoropropylene oxide derivatives of formula (I) is prepared by reacting an oligohexafluoropropylene oxide carbonyl fluoride of the general formula (II):

(II)

wherein Rf and n are as defined above with a metal iodide of the general formula (III):

(III)

wherein M is a metal atom and letter a is the valence of the metal atom.

The oligohexafluoropropylene oxide carbonyl fluorides of formula (II) may be prepared by any conventional well-known methods as disclosed in U.S. Pat. Nos. 3,250,808 and 3,322,826.

The metal iodides of formula (III) include alkali metal iodides such as LiI and NaI, alkaline earth metal iodides such as $MgI_2$ and $CaI_2$, and other metal iodides such as $AlI_3$. The metal iodide is preferably used in such amounts that the molar amount of iodine in the metal iodide is 1 to 1.2 times the moles of the oligohexafluoropropylene oxide carbonyl fluoride of formula (II). For example, the alkali metal iodide is 1 to 1.2 mol and the alkaline earth metal iodide is 0.5 to 0.6 mol per mol of the formula (II) compound.

These reactants are reacted, for example, by adding a polar solvent to the oligohexafluoropropylene oxide carbonyl fluoride of formula (II) and with stirring, aging thereto the metal iodide of formula (III) in increments. The preferred polar solvents used herein are aprotic solvents such as diethyl ether, diisopropyl ether, dibutyl ether, and acetonitrile. The solvents are preferably used in amounts of about 2 to 10% by weight of the alkali metal iodide or about 4 to 20% by weight of the alkaline earth metal iodide. The reaction temperature generally ranges form 0° C. to 100° C., preferably 20° C. to 50° C. and the reaction time generally ranges from about 2 to about 50 hours, preferably from about 5 to about 10 hours. Since both the reactants and the product are prone to hydrolysis, it is recommended to thoroughly purge the reactor with an inert gas such as nitrogen and argon. At the end of reaction, the metal fluoride is removed by filtration and then, the oligohexafluoropropylene oxide derivative of formula (I) can be recovered from the reaction solution in high yields by distillation isolation or by distilling off the solvent.

The resultant oligohexafluoropropylene oxide derivative of formula (I) can be readily converted into an iodine-containing oligohexafluoropropylene oxide of formula (IV) in high yields simply by exposing the former to UV, causing it to release carbon monoxide as shown by the following reaction scheme.

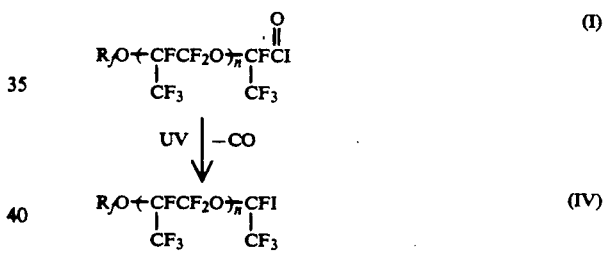

For UV exposure, a UV irradiation apparatus having a high pressure mercury lamp with a cooling quartz jacket may be used. Reaction is conducted by exposing the charge in the photo-reactor to UV at a wavelength of 180 to 380 nm, preferably 200 to 300 nm at a temperature of 0° to 60° C., preferably room temperature for about 2 to about 30 hours. There is no need for solvent although the charge may be diluted with a stable organic solvent if desired. Such solvents are perfluorooctane, perfluoroisononane and the like. Also preferably, this reaction is effected in an inert gas atmosphere such as nitrogen and argon.

The iodine-containing oligohexafluoropropylene oxides of formula (IV) obtained in this way are useful intermediates for the synthesis of fluoro resins, fluoro rubbers and fluoro surfactants.

There have been described oligohexafluoropropylene oxide derivatives of formula (I) which are useful intermediates for the synthesis of iodine-containing oligohexafluoropropylene oxides of formula (IV) which are, in turn, useful source materials for the synthesis of fluoro resins, fluoro rubbers and fluoro surfactants. The method of the invention is successful in producing oligohexafluoropropylene oxide derivatives of formula (I) in a commercially advantageous manner in high yields.

EXAMPLE

Examples of the present invention are given below by way of illustration and not by way of limitation.

EXAMPLE

A ½-liter four-necked flask equipped with a mechanical stirrer, reflux condenser, and gas inlet tube was charged with 400 grams (0.80 mol) of a carboxylic fluoride of the formula:

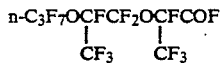

n-C$_3$F$_7$OCFCF$_2$OCFCOF
 | | 
 CF$_3$ CF$_3$ and 8 grams of acetonitrile. With stirring the contents, 118 grams (0.88 mol) of lithium iodide was added to the flask in several portions in an argon stream. The lithium iodide was added in such a controlled rate that the temperature of the contents did not exceed 40° C. At the end of addition, the contents were stirred for a further 15 hours.

The contents were passed through a glass filter to remove the solids. Distillation of the filtrate yielded 421 grams of a fraction having a boiling point of 87°–90° C./80 mmHg. The yield was 87%.

The product was analyzed by elemental analysis, GC-MS, IR spectroscopy, and $^{19}$F-NMR. The results are shown below.

| Elemental analysis | C | F | I | O |
| --- | --- | --- | --- | --- |
| Calcd., % | 17.82 | 53.30 | 20.96 | 7.92 |
| Found, % | 17.79 | 53.37 | 20.91 | 7.93 |

GC-MS m/e (M+) molecular weight 606

IR spectroscopy

FIG. 1 is a chart showing the IR spectrum of the product. It is observed that the absorption peak at 1890 cm$^{-1}$ attributable to —CO—F disappeared and a peak newly developed at 1785 cm$^{-1}$ attributable to —CO—I.

$^{19}$F-NMR

δ (ppm): 66.5 (m, 1F, CF), 52.8 (m, 2F, CF$_2$), 41.0 (m, 1F, CF—COI), −1.5–7.1 (m, 13F, —CF$_3$, CF$_2$O—).

With these measurement results, the product was identified to be a compound of the following formula.

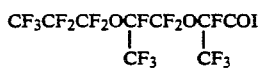

CF$_3$CF$_2$CF$_2$OCFCF$_2$OCFCOI
 | | 
 CF$_3$ CF$_3$

Reference Example

A UV irradiation apparatus was equipped with a high pressure mercury lamp with a cooling quartz jacket. The apparatus was charged with 200 grams (0.33 mol) of the compound of Example, which was exposed to UV light while stirring with a magnetic stirrer. The lamp was operated at a power of 100 W and a wavelength of 220 to 380 nm. Reaction was continued for 16 hours at 35° to 40° C. in an argon stream. At the end of reaction, the reaction product was distilled, obtaining 181 grams of a fraction having a boiling point of 78.5° C./101 mmHg. The yield was 95%.

The product was analyzed by elemental analysis, GC-MS, IR spectroscopy, and $^{19}$F-NMR. The results are shown below.

| Elemental analysis | C | F | I | O |
| --- | --- | --- | --- | --- |
| Calcd., % | 16.61 | 55.88 | 21.79 | 5.54 |
| Found, % | 16.57 | 55.91 | 21.92 | 5.60 |

GC-MS m/e (M+) molecular weight 578

IR spectroscopy

Figure 2:
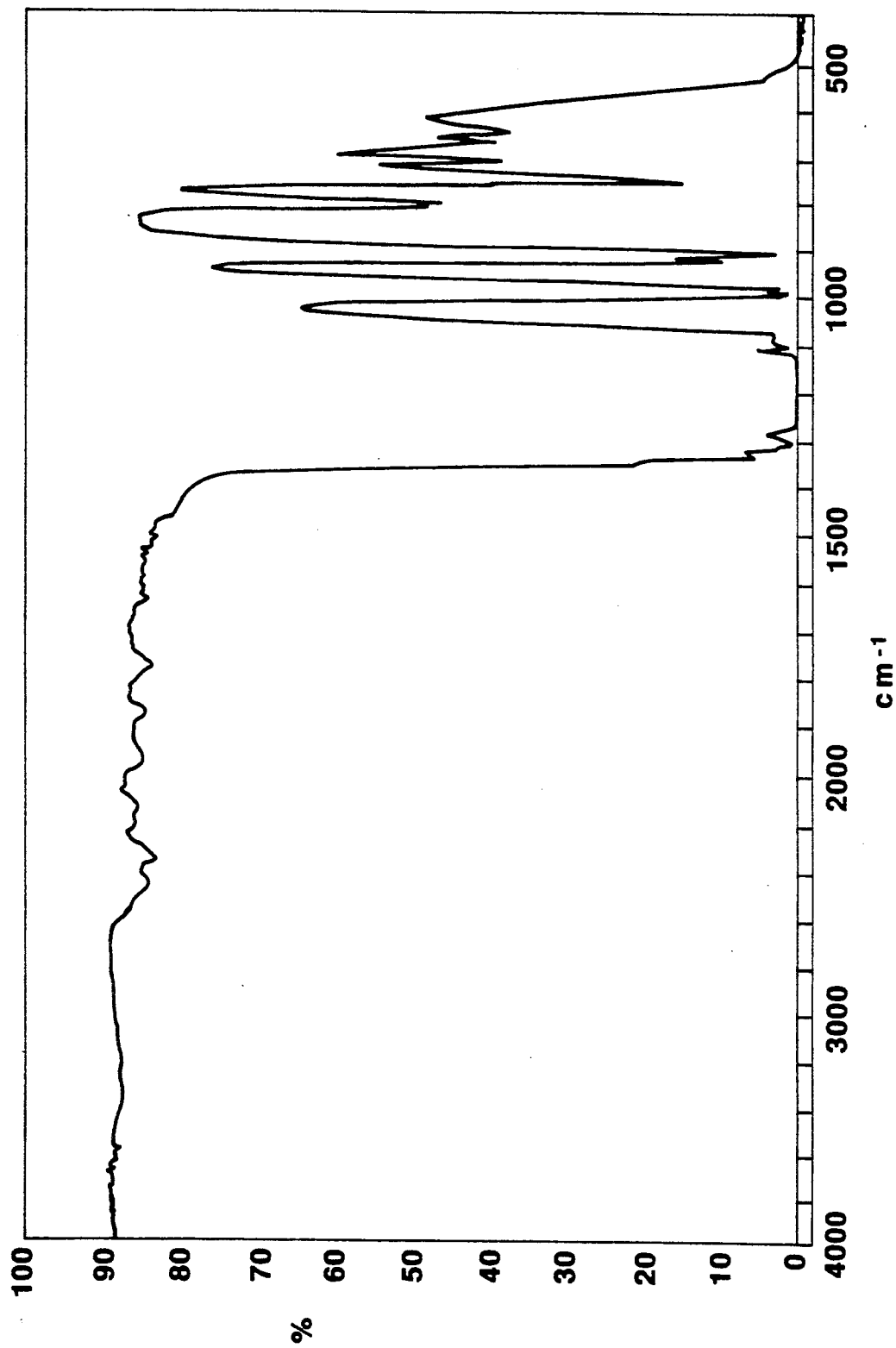
FIG. 2 is a chart showing the IR spectrum of an iodine-containing oligohexafluoropropylene oxide obtained in Reference Example.

FIG. 2 is a chart showing the IR spectrum of the product. It is observed that the absorption peak at 1785 cm$^{-1}$ attributable to —CO—I disappeared.

$^{19}$F-NMR

δ (ppm): 69.9 (m, 1F, CF), 59.8 (m, 2F, CF$_2$), 3.7–15.8 (m, 13F, —CF$_3$, —CF$_2$O—). -0.3 (m, 1F, —CFI)

With these measurement results, the product was identified to be a compound of the following formula.

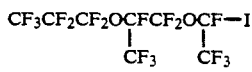

CF$_3$CF$_2$CF$_2$OCFCF$_2$OCF—I
 | | 
 CF$_3$ CF$_3$

We claim:

1. An oligohexafluoropropylene oxide derivative of the general formula (I):

(I)

wherein Rf is a perfluoroalkyl group having 1 to 10 carbon atoms and letter n is an integer of from 0 to 100.

2. A method for preparing an oligohexafluoropropylene oxide derivative of the general formula (I):

(I)

wherein Rf is a perfluoroalkyl group having 1 to 10 carbon atoms and letter n is an integer of from 0 to 100, said method comprising the step of reacting an oligohexafluoropropylene oxide carbonyl fluoride of the general formula (II):

(II)

wherein Rf and n are as defined above with a metal iodide of the general formula (III):

MI$_a$  (III)

wherein M is a metal atom and letter a is the valence of the metal atom.

* * * * *